United States Patent [19]
Henley

[11] Patent Number: 5,823,990
[45] Date of Patent: Oct. 20, 1998

[54] ULTRASONIC LIPOSUCTION HANDPIECE

[76] Inventor: Julian L. Henley, 38 Munger Rd., Guilford, Conn. 06437

[21] Appl. No.: 783,875

[22] Filed: Jan. 16, 1997

[51] Int. Cl.⁶ .................................................. A61B 17/22
[52] U.S. Cl. ............................. 604/22; 606/167; 606/180
[58] Field of Search ............................... 604/22; 128/751, 128/752, 753–758; 606/167, 169, 170, 171

[56] References Cited

U.S. PATENT DOCUMENTS

| | | | |
|---|---|---|---|
| 5,275,607 | 1/1994 | Lo et al. | 604/22 |
| 5,441,510 | 8/1995 | Simpson et al. | 604/22 |
| 5,514,115 | 5/1996 | Frantzen et al. | 604/22 |

*Primary Examiner*—Manuel Mendez
*Attorney, Agent, or Firm*—Michael G. Petit

[57] ABSTRACT

An ultrasonic avulsing liposuction handpiece including a handle portion and a cannula portion. In one embodiment, the cannula portion includes an auger rotatably mounted within an apertured outer tube. An independently controllable source of vibration housed within the handpiece causes the auger to vibrate at a desired frequency as the auger rotates. A portion of the rotary auger underlying an aperture in the wall of the outer tube includes a helical flange which has an elastically deformable outer tissue-contacting edge. When the outer tube is inserted within fatty tissue, the tissue-contacting edge avulses or tears apart fatty tissue protruding inwardly through the aperture in the outer tube when the auger is rotating. The mechanical vibration imparted to shaft of the rotating auger enhances the mechanical transport of avulsed tissue to a vacuum aspirator port within the handpiece for removal. The handpiece is relatively easy to use, rendering the procedure less tiring for the surgeon. In all embodiments incorporating vibration, the tissue-removing element vibrates at an ultrasonic or sonic frequency within the protective confines of the outer tube thereby reducing loading and heating. In the avulsing auger embodiment, the rotating auger vibrates within the outer tube, imparting a complex, wobbly, vibrorotatory wavelike motion to the tissue-contacting edge of the auger providing improved performance for suction lipectomy procedures.

4 Claims, 2 Drawing Sheets

ULTRASONIC LIPOSUCTION HANDPIECE

BACKGROUND OF THE INVENTION

1. Field of the Invention

An apparatus for the selectively removing fatty tissue from beneath the skin of an animal and, more particularly, to an ultrasonic handpiece for performing power assisted suction lipectomy.

2. Prior Art

Suction assisted lipectomy, a procedure originally developed in France, was introduced to the United States over a decade ago. Since then, the procedure has rapidly spread in popularity and consumer demand. The procedure involves anesthetizing a portion of the body containing unwanted fat deposits, introducing an apertured suction cannula beneath the skin into the unwanted fat and tearing the tissue apart by repeatedly jabbing the tip of the cannula into the tissue thereby mechanically breaking up (avulsing) the fat. The avulsed fat cells are then aspirated by suction means. Continuous reciprocal stroking of the cannula mechanically disrupts fatty tissue, allowing additional fat to be removed. The repetitive stroking movement of a cannula is both tiring for the physician and traumatic and uncomfortable for the patient who, notwithstanding anesthesia, experiences pain and discomfort with each thrust. Since fat from various different portions of the body is normally removed during the procedure, and further in view of the intense discomfort of the procedure, adequate local anesthesia of every fat-containing operative site may not be achieved.

Various types of manually powered liposuction cannulas, some disposable and some reusable, are commercially available. Liposuction cannulas are provided in different lengths and diameters, each having different slot or aperture dimensions to meet particular needs. Some apertures are configured in the "cobra head" configuration to increase the surface area of the cannula aperture while other cannulas employ a plurality of openings or apertures in the outer wall of the cannula, each aperture being operable for severing any tissue projecting into the aperture when the cannula is moved in the direction of its long axis. In each case the metal cannula is introduced into the (anesthetized) fat bearing target area through an incision in the skin. Powerful suction pulls some of the surrounding fat into the hollow cannula through one or more apertures and the thrusting movement of the cannula either avulses or severs a portion of such fat from the surrounding tissue. Adipose tissue has a low tensile strength compared to other tissues with which it is associated and the repetitive back and forth thrusting movement of the suction cannula differentially avulses large portions of fat from adjacent tissue within a given surgical area. This technique exploits the lower tensile strength of the fatty tissue and prevents excessive damage to the blood vessels due to perforation by the cannula since vascular structures comprise thicker collagen than fat and have greater tensile strength than fatty tissue. In operation, manual devices are physically demanding on the surgeon and traumatic to the patient.

Numerous power assisted lipectomy devices have been developed. Some such power assisted devices employ mechanical shearing devices deployed at or near the distal tip of the cannula to cut and remove fat from adjacent tissue. Others employ a cannula transmitting ultrasonic vibrations to the operative site to disperse or rupture fat cells adjacent to the cannula. A power assisted suction lipectomy device employing a rotary member housed within a cannula is described by Swartz in U.S. Pat. No. 4,932,935, the teachings of which patent is being incorporated herein by reference thereto. Swartz, in the aforesaid '935 patent, discloses an improved lipectomy handpiece which includes a cannula portion having an inner tube rotatably mounted within a concentric outer tube. The outer tube has an elongate slot in the surface thereof which contacts the tissue during lipectomy. The inner tube, which is rotatably mounted within the outer tube, has a spiral slot in the wall thereof disposed to underlie the slot in the outer tube. A motor housed within the handle of the cannula rotates the inner tube within the outer tube by means of a worm drive. The spiral slot of the inner tube, which underlies the elongate slot on the outer tube, presents a "moving hole" when viewed from outside the cannula. The "moving hole" provides a moving aperture through which fatty tissue surrounding the cannula may enter the inner tube thereafter to be pulled apart from surrounding tissue. The avulsed tissue is aspirated from the operative site through the hollow interior of the inner tube of the cannula into a removal port by suction means.

In an alternate embodiment, Swartz (U.S. Pat. No. 4,932, 935) discloses a cannula wherein the elongate slot in the outer cannula, which slot is disposed substantially coaxially with the long axis of the cannula, overlies a diagonal slot in the inner tube. Motor means within the handle of the cannula drives the inner tube in a rotary oscillatory motion with respect to the outer tube causing the "traveling hole" to move back and forth within the slot of the outer cannula rather than appearing at one end of the slot and disappearing at the other end only to reappear at the first end of the slot upon completion of a full rotation. The edges of the slots on both the inner and the outer tubes are provided with rounded edges to prevent unnecessary cutting of tissue. The round metal edges bordering the slots on the inner and the outer tubes pinch tissue which projects therebetween. This pinching and pulling avulses a portion of the tissue without applying sufficient force to avulse tissue having higher tensile strength. The Swartz device reduces trauma to the patient by preserving the integrity of non-target tissue while providing enhanced selectivity for removing fatty tissue.

The above described cannulas remain the mainstay of the suction lipectomy surgical instrumentarium and such prior art cannulas allow the operating surgeon to remove fat more or less differentially; sparing some of the larger blood vessels from injury. Although smaller blood vessels are traumatized by the force required for fat removal using the equipment presently available and a certain amount of bleeding occurs, this elective procedure has generally proven itself to be relatively safe and effective in accomplishing the localized removal of fat in patients. Still, there exists a need for a power assisted liposuction handpiece which further reduces trauma to non-fatty tissue and is less tiring for the surgeon to use.

The present inventor has employed power assisted liposuction handpieces to facilitate suction lipectomy, and more particularly, has used ultrasound at power levels up to 150 watts as an adjunctive means for facilitating suction lipectomy and for reducing trauma to non-fatty tissue while performing the procedure. The marginal improvement in tissue specificity observed by employing ultrasonic assistance as an adjunctive tool during suction liposuction indicated the need for more efficient power assisted suction lipectomy equipment. Accordingly, the present inventor, in U.S. patent application Ser. No. 08/546,478, the content of which patent application is incorporated herein by reference thereto, discloses a power-assisted avulsing suction lipectomy handpiece which provides both improved tissue specificity during fat removal and ease of operation. The avulsing liposuction handpiece includes a handle portion and a cannula portion releasably attached to the handle portion. The cannula portion further comprises a tubular apertured outer tube having an auger concentrically and rotatably mounted within the outer tube. The radial edge of the rotating auger and the perimeter edge of the relatively stationary aperture in the outer tube, cooperate to avulse or pull apart tissue protruding into the cannula through the aperture in the outer tube. The stationary edge of the aperture and the rotating tissue-contacting edge of the rotating auger pinch and stretch the tissue, applying sufficient force to overcome cohesive forces within the tissue.

When the apertured cannula portion of the lipectomy device penetrates unwanted fatty tissue, the surgeon presses upon the overlying skin, the pressure forcing a portion of the fat adjacent to the aperture to bulge or herniate through the aperture into the interior of the cannula. The auger, rotating therewithin, presents an elastic tissue-contacting avulsing edge which grasps and avulses fatty tissue interposed and trapped between the moving avulsing edge of the auger and the perimeter of the aperture while sparing more cohesive tissue. As the cannula is introduced into a subcutaneous fat-bearing area, instead of the surgeon applying a reciprocal back and forth movement to avulse fat, the electric-powered rotary motion of the auger within the cylindrical apertured outer tube of the cannula produces a gradual controlled avulsion of fat cells protruding into the cannula through the aperture.

In view of the observed clinical advantages of avulsive liposuction to both the patient and surgeon, it is desirable to even further improve the avulsive suction lipectomy device of the prior art, providing enhancements thereto which improve tissue specificity and ease of use while further reducing trauma to the patient.

SUMMARY OF THE INVENTION

It is a primary object of this invention to provide an improved handpiece for performing power-assisted suction lipectomy.

It is another object of the invention to provide a handpiece for performing power-assisted lipectomy device which, in operation, selectively removes fatty tissue thereby reducing trauma to non-fatty tissue.

It is still another object of the invention to provide a handpiece for a power assisted suction lipectomy device which reduces damage to nerves and vascular tissue during suction lipectomy.

It is yet another object of the invention to provide a handpiece for power assisted liposuction which reduces both heat generation within the handpiece and power loss during suction lipectomy.

It is an object of the invention to provide a power-assisted avalsive liposuction handpiece which further includes vibratory means operable for causing a tissue-contacting avulsing edge within the handpiece to vibrate at a desired frequency.

Further objects, features and advantages of the invention will become apparent upon consideration of the following detailed disclosure of the invention especially when it is taken in conjunction with the accompanying drawings wherein:

DESCRIPTION OF THE PREFERRED EMBODIMENTS

The invention is a modified handpiece adapted to use vibrational energy, preferably in the range 10 Hz–100 KHz, as an adjunctive force for performing power-assisted avulsive liposuction. The principal mechanism responsible for the removal of fat is avulsion by an auger rotating within an apertured tube. The handpiece is adapted to superimpose a relatively high frequency vibrational motion upon the rotary motion of the avulsing member. The superimposition of the vibratory motion to a rotating auger imparts a complex vibroratory motion to the avulsing edge of the rotating member. By enclosing the vibrating tissue-avulsing member within an outer tube, the present invention advantageously restricts the region of contact between solid tissue and the vibrating member to the avulsing edge portion. The vibroratory motion of the avulsing edge assists avulsive action for fat removal without compromising more tenancies tissue.

Figure 1:
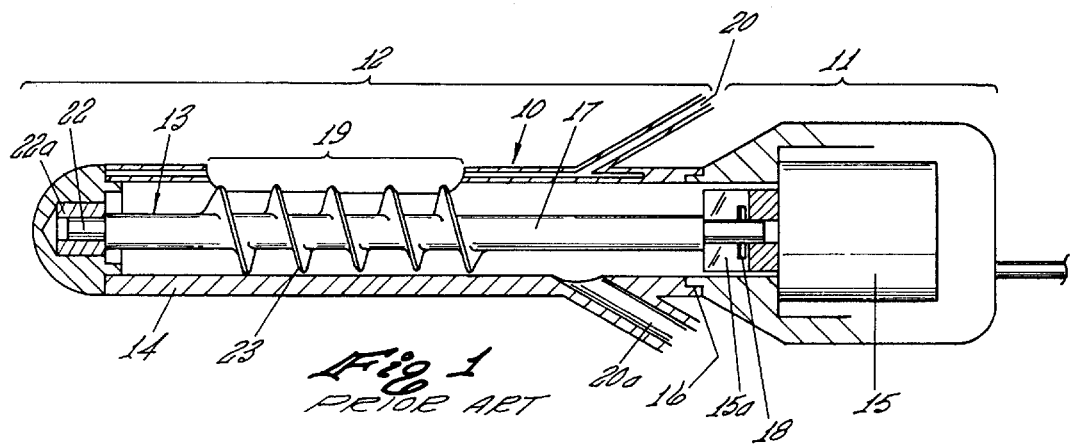
FIG. 1 is a partially cut-away side view of the power assisted suction lipectomy handpiece of the present invention showing the handle portion, the cannula portion, including vacuum aspiration and irrigating ports.

Although the adjunctive use of mechanical vibrational energy may be adapted to enhance performance of various power assisted and manually powered avulsive suction lipectomy devices, the modification of an avulsive liposuction handpiece employing a power assisted rotating auger to include an independent adjunctive vibratory motion is presented as an exemplary embodiment of such a device. With reference first to FIG. 1, a handpiece 10 for performing power-assisted avulsive suction lipectomy in accordance with the prior art is shown in elevational cross-section. The handpiece 10 comprises a handle portion 11 and a cannula portion 12. The cannula portion 12 has a rotary member 13 rotatably mounted within an elongate apertured outer tube 14. A rotary motor 15 for driving member 13 is housed within the handle portion 11 of the handpiece 10.

Alternatively, a pneumatically or vacuum driven motor operable for supplying rotational power may be used to rotate the member 13 which is preferably an auger. A cable drive shaft from an external motor may also be employed to deliver rotary power to the rotating member. The speed of rotation of the rotary motor 15 is preferably controlled by a foot operable controlling means (not shown). Such speed control devices are well known in the art. The cannula portion 12 of the handpiece 10 is affixed to the handle portion 11 of the handpiece 10 by means of a releasable connector 16. The rotary member 13 housed within the cannula portion 12 has a central shaft 17 having coupling means 18 on the proximal end of the shaft 17 operable for releasably attaching the shaft 17 of the rotary member 13 to the drive shaft connector means 15a on the distal end of the motors 15 drive shaft within the handle portion.

Figure 2:
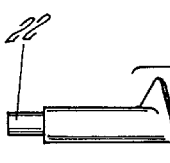
FIG. 2 is a side elevational view of the elastically deformable rotary member shown in FIG. 1.
Figure 3:
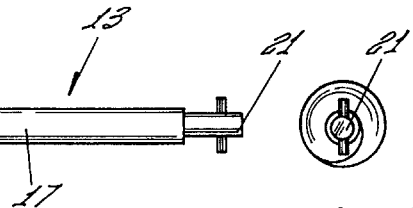
FIG. 3 is an end on view of the rotary member of FIG. 2 viewed in the direction from right to left.

An elevational view of the rotatable member 13 of the cannula portion 12 of the handpiece 10 is shown in FIG. 2. The rotary member 13 is an auger having an axial shaft 17 with a proximal end 21 and a bearing 22 at the distal end and auger portion 23. The auger portion 23 of the rotary member 13 is dimensioned to be at least as long as the overlying aperture 19 in the outer tube portion 14 of the cannula. The proximal end of the auger portion, as shown in FIG. 3, has releasable connector means 21 thereon operable for attachment to mating attachment means 15a on the distal end of the drive shaft of the rotary motor (not shown in FIG. 2).

Figure 4:
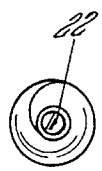
FIG. 4 is an end view of the rotary member of FIG. 2 viewed from left to right.

FIG. 4 is an end-on view of the rotary member 13 of FIG. 2, viewed from left to right, showing the bearing 22 at the distal end of the auger shaft 17. The stabilizing bearing 22 on the distal end of the auger shaft rotatably engages an axially disposed bearing seat 22a (FIG. 1) axially on the distal end of the outer tube 14 which bearing 22 provides support for the rotary member 13. The important feature of the prior art avulsive liposuction handpiece shown in FIGS. 1–4 is that the avulsing portion of the cannula is capable of elastic deformation. The avulsive portion of the cannula consists of the tissue-contacting radially outermost edge of the rotary member and the edge or rim of the aperture perimeter between which edges unwanted fatty tissue is entrapped and avulsed. The elastic deformability of the avulsive portion selectively reduces and may entirely eliminate damage to non-fatty tissue having a tensile strength greater than fatty tissue. Tissue having a lower tensile strength which becomes entrapped within the avulsive portion of the cannula will be pulled apart by the shear force caused by the relative motion of the corrugated tissue-contacting avulsing edge of the rotating member pulling one surface of the tissue in the direction of rotation while the opposing surface of the entrapped stretched film of tissue is held stationary, adhering to the overlying avulsing edge of the aperture by means of friction which generates heat which may be considerable and require cooling. The exemplary prior art avulsive suction lipectomy device described above requires rotation of the auger in only a single direction for avulsing fatty tissue during lipectomy. The rotary motor within the handle portion of the device will generate heat. Such heat can be dissipated by means of a heat exchanger (not shown) mounted on the handle portion in thermal contact with the portion of the handle portion overlying the rotary motor. The heat exchanger may simply comprise an irrigation fluid flow channel as shown at Numeral 20 in FIG. 1 which conducts a cooling fluid to the avulsive portion adjacent the aperture. The coolant fluid is removed by suction through the aspiration port 20a.

As mentioned above, the avulsive portion of the cannula also generates heat due to friction. The rate of heat generation may be minimized by performing the lipectomy procedure slowly. The heat generated at the avulsive edge can be reduced by the superposition of an axially directed vibratory motion upon the rotary motion of the auger shaft.

Figure 5:
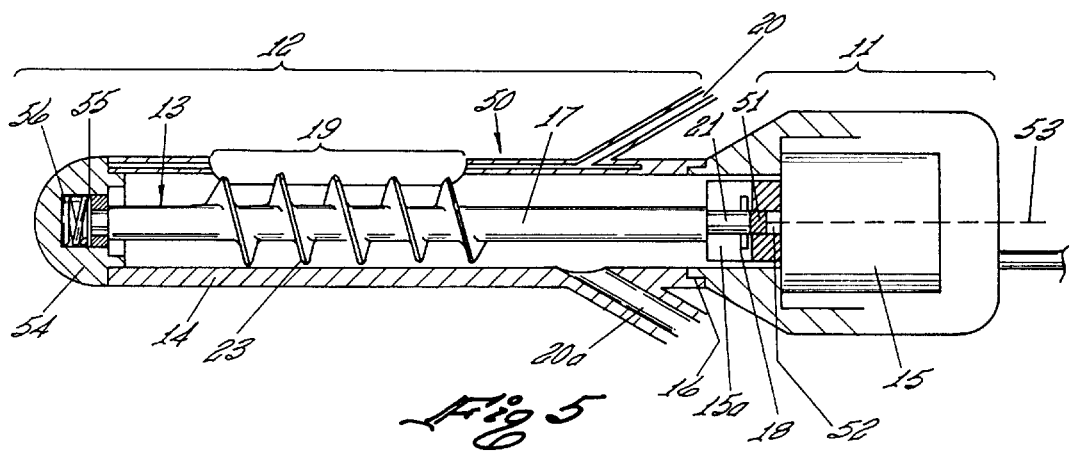
FIG. 5 is a partially cut-away side view of the ultrasonically assisted avulsing of the present invention showing the handle portion, the cannula portion and the vibrating element disposed to cause the shaft of the auger to mechanically vibrate.

With reference now to FIG. 5, which presents a cross-sectional elevational view of an embodiment 50 of an ultrasonic avulsive liposuction "avulsonic" handpiece in accordance with the present invention which employs a rotatable auger 13 in combination with the rim of an overlying aperture 19 for avulsion of fat and an axial shaft 12 thereon. The handpiece 50 has many of the features common to the prior art device shown in FIG. 1 except that a piezoelectric vibrating device 51 is inserted between a hollowed-out motor drive shaft 52 and the proximal end 21 of the rotating member 13. The piezoelectric crystal 51 receives power for oscillation from a power source (not shown) through an electrically conductive wire 53 which is passed through the lumen the hollowed-out motor drive shaft 52 to contact one electrode of the piezoelectric device. The other electrode of the device is grounded. The power source for the piezoelectric crystal is an oscillator driven at a frequency specific to the particular crystal being driven.

The distal end of the auger 13 has a bearing element 22 which presses against a distal end bearing surface 55. The bearing surface 55, in turn, is urged against the distal bearing 22 by means of a spring 56 disposed within the bearing seat 54 on the distal end of the outer tube 14. The compressive spring 56 urges the piston 55 towards the proximal end of the handpiece thereby pressing the shaft the proximal end 21 of the shaft 17 against the vibrating element 51.

Figures 6, 7:
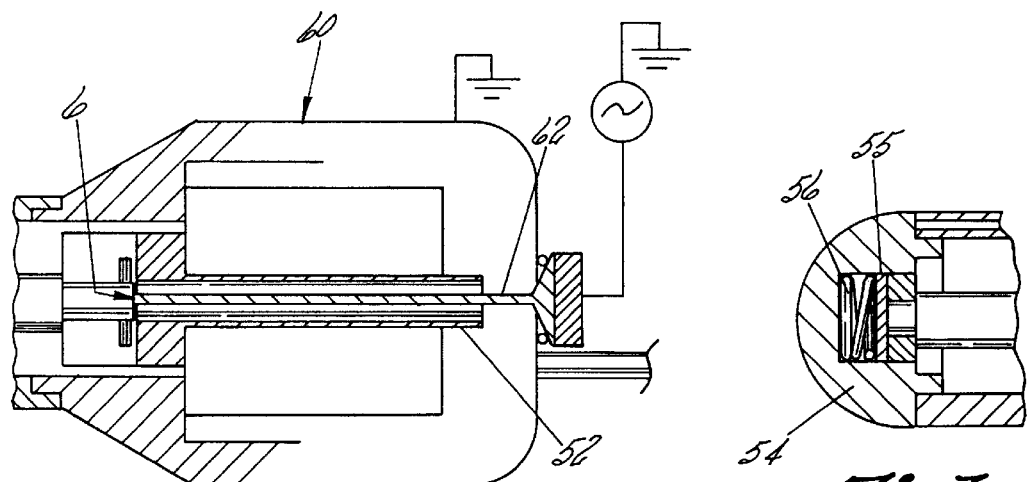
FIG. 6 is a cross-sectional overview of the handle portion of an embodiment of the present handpiece wherein the drive shaft of the rotary motor is hollow and accommodate a longitudinally vibrating rod coaxially mounted therewithin and extending therethrough wherein the rod provides vibratory communication between the stationary piezoelectric vibrating driver and the rotatably mounted shaft of the auger.
FIG. 7 is a partially cutaway side view of the distal end of the cannula showing the auger shaft support bearing and spring tensioning assembly.

An embodiment of the handpiece 50 which incorporates a piezoelectric device positioned outside of the casing and accessible for changing is shown in FIG. 6. The handle portion 60 includes the piezoelectric crystal 51 as in the embodiment shown in FIG. 5 above; however the piezoelectric crystal is housed outside of the motor rearwardly of the drive shaft 52 and in vibrational communication therewith. The piezoelectric crystal 53 receives power for operation from an oscillator 61 providing an electrical signal of the correct frequency for operating crystal. A rod 62 has a proximal end which abuts the piezoelectric crystal 53 on the approximal side and rests on a compressible O-ring 63 on the distal side. An extension of the rod passes through the hollow drive shaft 52 of the motor 15 to emerge proximally and pressed against the proximal end 21 of the overshaft 17. The distal end of the shaft 17 has a distal bearing portion 22 which bears against a piston 55 which is dimensioned to slide within a cylindrical chamber in the distal end of the outer tube. The bearing surface 55 is urged towards the proximal end of the handpiece by means of the spring 56 within the chamber.

Figure 8:
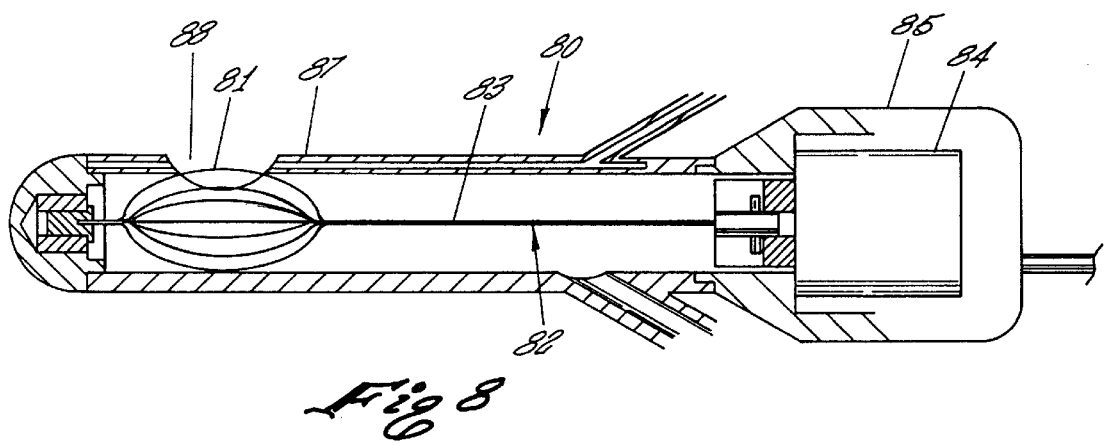
FIG. 8 is a cross-sectional, longitudinal view of an embodiment of an avulsing liposuction device employing an egg beater to provide an avulsing edge which rotates with respect to an aperture in the outer tube and which may be adapted to mechanically vibrate at ultrasonic frequency as it rotates.

FIG. 8 is a cross-sectional, longitudinal view of an embodiment of an avulsing liposuction device 80 employing the bulbous wire basket 81 an "egg beater" 82 to provide an avulsing edge. The shaft 83 of the egg beater 82 is rotatably driven by a motor 84 within the handpiece 85. The rotating shaft causes the wire basket 81 to rotate with respect to the aperture 86 in the outer tube 87. As with the previous embodiment of the avulsing liposuction device, this embodiment 80 may be adapted to mechanically vibrate at sonic or ultrasonic frequencies as it rotates by coupling a suitable driving means such as a piezoelectric device to the shaft 83.

Figure 9:
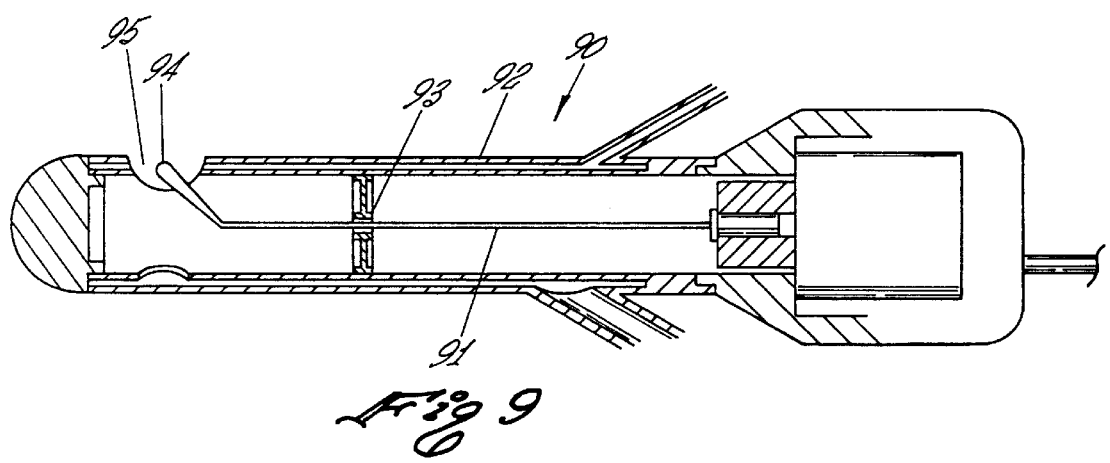
FIG. 9 is an embodiment of an ultrasonic assisted liposuction device wherein the ultrasonic vibrating element is enclosed within an outer tube and fat is presented to the tip through an aperture in the outer tube.

FIG. 9 is an embodiment 90 of an ultrasonic assisted liposuction device wherein the ultrasonic vibrating element 91 does not rotate but is enclosed within an apertured outer tube 92 and supported and stabilized therewithin by means of an elastic bushing 93 positioned at a vibratory mode. Fat is presented to the vibrating tip 94 through an aperture 95 in the wall of the outer tube 92.

The cannula portion of the various embodiments of the ultrasonic liposuction device in accordance with the present invention is preferably made in different lengths and diameters for different suction lipectomy applications. The overall diameter of the apertured outer tube of the cannula portion is preferably between 4 mm and 8 mm. Different sizes of cannulas are necessary because surgeons have different cannula preferences for performing suction lipectomy within different anatomical locations. As an example, the smaller cannulas have greater utilization for aspiration of fat under the neck, whereas larger, longer cannulas are used for abdominal fat aspiration as well as lateral thighs. The handpiece preferably has irrigation and aspiration ports integral therewith and operable for conducting irrigation solution to the cannula aperture as well as removing avulsed tissue from the cannula by vacuum aspiration.

While particular embodiments of the present invention have been illustrated and described, it would be obvious to those skilled in the art that various other changes and modification can be made without departing from the spirit and scope of the invention. For example, the avulsing efficiency of an avulsing edge in accordance with the handpiece of the present invention may also be varied by changing the density, shape and length of the grooves on the avulsing edge or texture applied thereto. Similarly, the present handpiece can be advantageously used in combination with adjunctive means for enhancing the efficiency and selectivity of fat removal including ultrasonic perturbation of the target tissue either before or during liposuction or the administration of an agent which reduces the cohesiveness of fatty tissue with respect to the cohesiveness of non-fatty associated tissue. It is therefore intended to cover in the appended claims all such changes and modifications that are within the scope of this invention.

What I claim is:

1. A handpiece comprising an invasive cannula portion and a non-invasive handle portion, said handle portion comprising an elongate case having a proximal end, a distal end, a housing, a vibrating member therewithin, a motor means adapted to rotate a drive shaft, and a power connector adapted to provide releasable connection of said handle portion to an external source of energy, said distal end of said handle portion having cannula connection means thereon, the invasive cannula portion comprising:

(a) a rigid elongate outer tube having (i) a proximal end having handle connector means thereon adapted to releasably engage said cannula connection means on said handpiece and (ii) a distal end and a hollow cylindrical wall enclosing an axial lumen therebetween, said cylindrical wall having an aperture therein with a rim wherein said rim is a stationary avulsing edge;

(b) an elongate avulsing member coaxially disposed and rotatably mounted within said lumen of said outer tube, the outermost lateral extension a portion of said avulsing member being a movable avulsing edge, wherein said avulsing edge elastically deforms away from said stationary avulsing edge in response to pressure applied between said stationary avulsing edge and said movable avulsing edge.

2. A power assisted suction lipectomy device comprising a handpiece, said handpiece further comprising;

(a) a handle portion having electrical power connection means adapted for releasable connection to an external source of electrical power, a motor having a movable drive shaft connected to said power connection means therewithin; and (b) a cannula portion wherein said cannula portion further comprises;

i) a hollow outer tube having a proximal end with connection means adapted to releasably connect said outer tube to said handle portion, and a distal end and a cylindrical wall therebetween with an aperture therein having an elastically deformable edge; and ii) a movable member disposed within said outer tube having a proximal end adapted to releasably engage said drive shaft and a distal end and a movable edge therebetween wherein at least a portion of said movable edge underlies said aperture in said cylindrical wall of said outer tube; and iii) a member having an elastically deformable stationary edge affixed to said outer tube and wherein said stationary edge overlies and is in juxtaposition with said movable edge, and wherein said stationary edge is elastically deformable;

(c) a piezoelectric vibrating element housed within said handle portion, said vibrating element having a distal end and a proximal end, said proximal end being in electrical communication with said source of electrical power.

3. The power assisted suction lipectomy device in accordance with claim 2 wherein said movable edge is elastically deformable, said movable edge comprising a helical flange having an outer avulsing edge projecting laterally therefrom along a length of a elongate shaft, said shaft having a proximal end adapted to releasably connect to said handle portion, and a distal end.

4. The power assisted suction lipectomy device in accordance with claim 3 wherein said stationary edge is rigid.

* * * * *